United States Patent [19]
Levy et al.

[11] Patent Number: 5,372,716
[45] Date of Patent: * Dec. 13, 1994

[54] SUPERCRITICAL FLUID EXTRACTION COUPLED TO ANALYTICAL CHROMATOGRAPHY SYSTEM

[75] Inventors: Joseph M. Levy, Gibsonia; Raymond K. Houck, Oakmont, both of Pa.

[73] Assignee: Suprex Corporation, Pittsburgh, Pa.

[ * ] Notice: The portion of the term of this patent subsequent to Apr. 27, 2010 has been disclaimed.

[21] Appl. No.: 929,727

[22] Filed: Aug. 13, 1992

Related U.S. Application Data

[63] Continuation-in-part of Ser. No. 662,255, Feb. 28, 1991, Pat. No. 5,205,987.

[51] Int. Cl.$^5$ .............................................. B01D 15/08
[52] U.S. Cl. .................... 210/198.2; 210/634; 210/656; 210/659
[58] Field of Search ............... 210/634, 635, 656, 659, 210/198.2; 422/70, 285

[56] References Cited

U.S. PATENT DOCUMENTS

| | | | |
|---|---|---|---|
| 3,686,117 | 8/1972 | Lauer | 210/198.2 |
| 4,070,284 | 1/1978 | Fujita | 210/659 |
| 4,137,161 | 1/1979 | Shimada | 210/659 |
| 4,271,099 | 6/1981 | Kukla | 138/40 |
| 4,271,697 | 6/1981 | Mowery | 210/659 |
| 4,478,720 | 10/1984 | Perrut | 210/659 |
| 4,484,061 | 11/1984 | Zelinka | 210/198.2 |
| 4,500,432 | 2/1985 | Poole | 210/659 |
| 4,554,436 | 11/1985 | Chlosta | 210/657 |
| 4,597,943 | 7/1986 | Sugiyama | 210/659 |
| 4,787,406 | 11/1988 | Edwards | 137/1 |
| 4,806,250 | 2/1989 | Takata | 210/659 |
| 4,814,089 | 3/1989 | Kumar | 210/659 |
| 5,009,778 | 4/1991 | Nickerson | 210/198.2 |
| 5,013,443 | 5/1991 | Higashidate | 210/634 |
| 5,094,741 | 3/1992 | Frank | 210/634 |

(List continued on next page.)

FOREIGN PATENT DOCUMENTS

| | | | |
|---|---|---|---|
| 416228 | 7/1925 | Germany | 137/1 |
| 582032 | 11/1946 | United Kingdom | 251/8 |

OTHER PUBLICATIONS

Ashrof-Khorossani, Journal of Chromatographic Science, vol. 28, Nov. 1990, pp. 599–604.

(List continued on next page.)

*Primary Examiner*—Ernest G. Therkorn
*Attorney, Agent, or Firm*—Ansel M. Schwartz

[57] ABSTRACT

The present invention is a collection system for use with supercritical fluid extraction. The system comprises a device for collecting analyte from a fluid having the same. There is also a restrictor for controlling flow of analyte to the collecting device. The restrictor converts the fluid with analyte from a first pressure to a second pressure. The second pressure is less than the first pressure. The first pressure is a supercritical pressure. The restrictor is in fluidic communication with the collecting device. There is also a device for deabsorbing the analyte from the collecting device. The deabsorbing device is in fluidic communication with the collecting device. The collection system also includes a chromatograph for analyzing the analyte. The chromatograph is in fluidic communication with the collecting device to receive deabsorbed analyte. The chromatograph is remote from the collecting device. The chromatograph can be either a gas chromatograph or a liquid chromatograph. In one embodiment of the collection system, the deabsorbing device backflushes deabsorbing fluid through the collecting device into the chromatograph. That is, the flow of fluid during deabsorbing is in an opposite direction to the flow of fluid during collection. Alternatively, the deabsorbing device foreflushes the deabsorbing fluid through the collecting device into the chromatograph. That is, the flow of fluid during deabsorbing is the same direction as the flow of fluid during collection.

18 Claims, 5 Drawing Sheets

U.S. PATENT DOCUMENTS

| | | | |
|---|---|---|---|
| 5,116,508 | 5/1992 | Kumar | 210/634 |
| 5,133,859 | 7/1992 | Frank | 210/634 |
| 5,139,681 | 8/1992 | Cortes | 210/659 |
| 5,147,538 | 9/1992 | Wright | 210/634 |
| 5,152,176 | 10/1992 | Bryselbout | 73/23.41 |
| 5,180,487 | 1/1993 | Saito | 210/659 |
| 5,198,115 | 3/1993 | Stalling | 210/634 |
| 5,205,154 | 4/1993 | Lee | 73/23.35 |
| 5,205,987 | 4/1993 | Ashraf-Khorassani | 210/634 |

OTHER PUBLICATIONS

Snyder, Introduction to Modern Liquid Chromatography, John Wiley & Sons, Inc., New York, 1979, pp. 203–204.

Levy, The Use of Alternative Fluids in On–line Supercritical Fluid Extraction–Capillary Gas Chromatography, Journal of High Resolution Chromatography, vol. 14, 1991, pp. 661–666.

Levy "On–line Multidimensional Supercritical Fluid/Capillary Gas Chromatography", Journal of High Resolution Chromatography & Chromatography Communications, vol. 10, 1987, pp. 337–341.

Levy, "Supercritical Fluid Extraction Coupled to Gas and Supercritical Fluid Chromatography," LC–GC, the Magazine of Separation Science, vol. 10, No. 5 May 1992 pp. 386–391.

Cortes, "On-Line Coupling of Supercritical Fluid Extraction with Multi dimensional Microcolumn Liquid Chromatography/Gas Chromatography", Anal. Chem. 1991, 63, 2719–2724.

Raymer, "Development of a Flexible, On–line Supercritical Fluid Extraction–Gas Chromatographic (SFC–GC) System", Journal of Chromatographic Science, vol. 29, Nov. 1991, pp. 467–475.

SUPERCRITICAL FLUID EXTRACTION COUPLED TO ANALYTICAL CHROMATOGRAPHY SYSTEM

This is a continuation-in-part of U.S. patent application Ser. No. 07/662,255 filed Feb. 28, 1991, now U.S. Pat. No. 5,205,987.

FIELD OF THE INVENTION

The present invention is related to supercritical fluid extraction systems. More specifically, the present invention is related to a supercritical fluid extraction system directly coupled to either a liquid or gas chromatograph.

BACKGROUND OF THE INVENTION

Supercritical fluid extraction (SFE) is a sample preparation technique used to extract analytes of interest from a sample, for example, environmental pollutants from a soil sample. Some types of sample preparations must be performed for a wide range of environmental, food, polymer, petroleum, pharmaceutical and other classes of samples due to the complex nature of the sample. Many of these samples are so complex that they cannot be directly evacuated by analytical techniques such as gas chromatography (GC) or liquid chromatography (LC). The complex samples must first go through a sample preparation step to perform a gross separation of the analytes of interest from the matrix in which they are contained, for example, the environmental pollutants from soil. After the sample preparation step, then just the analytes of interest are analyzed by the analytical technique.

The most popular sample preparation steps are Soxhlet extraction and liquid extraction. An alternative to these types of extraction techniques is supercritical fluid extraction (SFE). SFE offers a relatively rapid, simple and inexpensive technique to perform sample preparations. The basis of SFE is that a fluid, such as carbon dioxide, is held at a specific pressure, temperature and flow rate, which is above its critical temperature and pressure and thus is a supercritical fluid, is passed through the matrix containing the analytes of interest. This matrix is contained in an extraction vessel. The fluid diffuses into the pores of the matrix, solubilizes the analytes of interest, and then carries the analytes away from the matrix. The analytes are then collected by some device, so that the analytes can be analyzed by some further analytical technique, such as chromatography. The matrix (now without analytes) is left behind in the extraction vessel. Supercritical fluids have favorable diffusivities and viscosities providing for good mass transfer characteristics. Their strength can be easily controlled, and since most are gases at ambient conditions. These are but a few of the advantages of supercritical fluid extraction.

Typically, an SFE system is comprised of a pump which pumps the supercritical fluid to an extraction vessel where analytes are extracted from a sample matrix. The analytes are then transported to a collection device and the supercritical fluid is depressurized to ambient pressure and is vented. The analysis of the collected analyte can be either "off-line", that is, remote from the collection device, or "on-line", that is, fluidically connected to the collection device. Overall "on-line" collection is a more simple collection method than off-line collection. The focus of the present invention is improvements in on-line SFE-chromatography collection and coupling techniques.

In the prior art, gas chromatographs have been connected on-line to SFE through the use of a transfer line with a restrictor at the end of the transfer line. The restrictor is placed through the septum of the GC inlet port and the analytes of interest are directly deposited into the GC inlet port which can be either a split-splitless GC injector or an on-column GC injector. The problem with this approach is 1) flow from the SFE is limited to about 0.3 ml/min. (liquid $CO_2$ equivalent) maximum flow, above this flow the collection capability of the method is overloaded, 2) when using an on-column injector, flow rates above 0.1 ml/min. (liquid $CO_2$ equivalent) usually causes the GC flame dector flame to blow out, 3) overall SFE sample size is limited due to the low flow rates. See J. M. Levy, E. Storozynsky, M. Ravey, "The Use of Alternative Fluids in On-Line Supercritical Fluid Extraction-Capillary Gas Chromatography", Journal of *High Resolution Chromatography*, Vol. 14, 1991, pp. 661–666; J. M. Levy, J. P. Guzowski, W. E. Huhak, "On-Line Multidimensional Supercritical Fluid Chromatography/Capillary Gas Chromatography", *Journal of High Resolution Chromatography & Chromatography Communications*, Vol. 10, 1987, pp. 337–341; and J. M. Levy, A. C. Rosselli, E. Storozynsky, R. Ravey, L. A. Dolata, M. Ashraf-Khorassani, "Supercritical Fluid Extraction Coupled to Gas and Supercritical Fluid Chromatography", *LC-GC, The Magazine of Separation Science*, Vol. 10, No. 5, May 1992, pp. 386–391.

Further examples of supercritical fluid extraction devices can be found in "Hernan J. Cortes, et al., On-Line Coupling of Supercritical Fluid Extraction with Multidimensional Microcolumn Liquid Chromatography/Gas Chromatography, *Anal. Chem.* 1991, 63, 2719–2724" and "J. H. Raymer, et al., Development of a Flexible, On-Line Supercritical Fluid Extraction—Gas Chromatographic (SFE-GC) System, Journal of Chromatographic Science, V29, November 1991, pp. 467–475."

The present invention has advantages over the prior art approach in the following ways: 1) since the collection step happens external to the GC inlet port, much higher flow rates of supercritical fluid can be used. For example, 3–5 ml/min. (compressed) or higher $CO_2$ flow rates can be used which allows for faster extractions, larger volume extraction vessels and much lower sensitivities. This results in the fact that more matrix can be easily extracted allowing low part per billion and even potentially part per trillion extractions to be performed, 2) since the collection step is decoupled from the GC injection port, the collection trap can be packed with other types of packing ($C_{18}$, etc.) allowing additional selectivity to be employed, and 3) since the collection step is decoupled from the GC injection port, the GC can be operated separately from the SFE system, allowing overall faster time of on-line SFE-chromatography analysis. Thus, the GC can be analyzing a sample while the SFE system is extracting the next sample.

In addition to the above benefits for gas chromatography, other benefits exist for liquid chromatography. Very little work has been done in the prior art to couple SFE to liquid chromatography due to the difficulties in the coupling of the techniques. Cortes, et al. shows one of the few approaches to SFE-LC coupling. This invention has advantages over the SFE-LC prior art in the following ways: 1) the collection step is decoupled from the LC injection step, thus the LC can be operated separately from the SFE system, allowing overall faster time of on-line SFE-LC analysis, 2) the collection means is separate from the LC column and of larger volume and thus capable of collecting a larger mass of analyte. This allows greater sensitivity in the extraction and also allows the use of a larger extraction vessel.

SUMMARY OF THE INVENTION

The present invention is a collection system for use with supercritical fluid extraction. The system comprises a device for collecting analyte from a fluid having the same. There is also a restrictor for controlling flow of analyte to the collecting device. The restrictor converts the fluid with analyte from a first pressure to a second pressure. The first pressure is a supercritical pressure. The second pressure is less than the first pressure. The restrictor is in fluidic communication with the collecting device. There is also a device for deabsorbing the analyte from the collecting device. The deabsorbing device is in fluidic communication with the collecting device. The collection system also includes a chromatograph for analyzing the analyte. The chromatograph is in fluidic communication with the collecting device to receive deabsorbed analyte. The chromatograph is remote from the collecting device. The chromatograph can be either a gas chromatograph or a liquid chromatograph.

In one embodiment of the collection system, the deabsorbing fluid backflushes through the collecting device and into the chromatograph. That is, the flow of the deabsorbing fluid during deabsorbing is in an opposite direction to the flow of supercritical fluid during collection. Alternatively, the deabsorbing fluid can foreflush the deabsorbing fluid through the collecting device into the chromatograph. That is, the flow of deabsorbing fluid during deabsorbing is the same direction as the flow of the supercritical fluid during collection.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
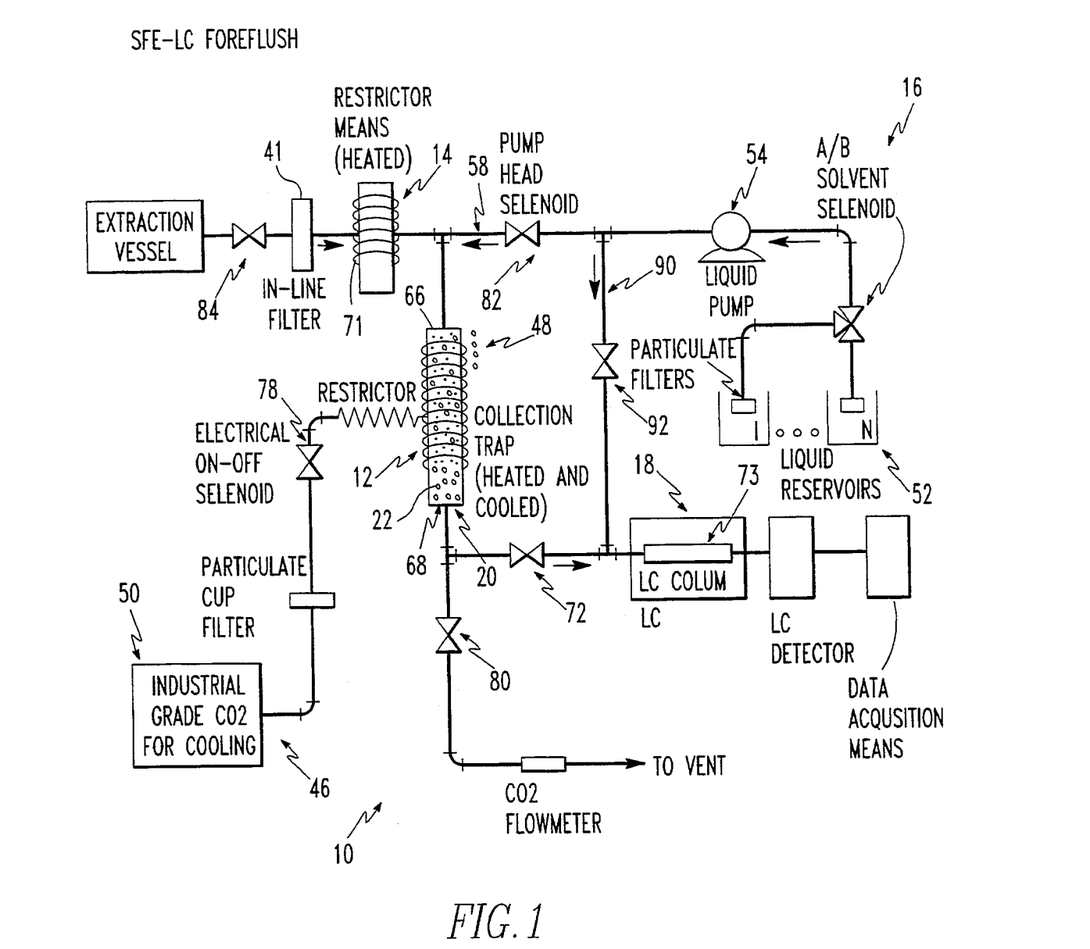
FIG. 1 is a schematic representation of an embodiment of the supercritical fluid extraction system operating in a foreflush mode to a liquid chromatograph.

Referring now to the drawings wherein like reference numerals refer to similar or identical parts throughout the several views, and more specifically to FIG. 1 thereof, there is shown a schematic representation of a collection system 10 for use with supercritical fluid extraction. The system 10 comprises a device 12 for collecting analyte associated with the supercritical fluid extraction. The system 10 is also comprised of a restrictor 14 for converting fluid with analyte from a high or supercritical pressure to a low pressure. Additionally, the system 10 is comprised of a device 16 for deabsorbing the analyte from the collecting device 12. The deabsorbing device 16 is in fluidic communication with the collecting device 12. The system 10 also includes a chromatograph 18 in fluidic communication with the collecting device 16 for analyzing the analyte. The chromatograph 18 is remote from the collecting device 12.

Preferably, the collecting device 12 includes a collection trap 20 in which the analyte is gathered. The collection trap 20 can include packing 22 disposed therein to increase the surface area upon which the analyte can be gathered. The packing 22 can be, for instance, steel balls, $C_{18}$, $NH_2$, CN, glass beads or silica to name but a few of the many possible types. The pressure rating of the trap 20 should be at least 200 atmospheres. It is preferably made out of stainless steel, although essentially any good thermal conducting material which is nonreactive with the analyte that is able to withstand such pressure can be used.

Figure 4:
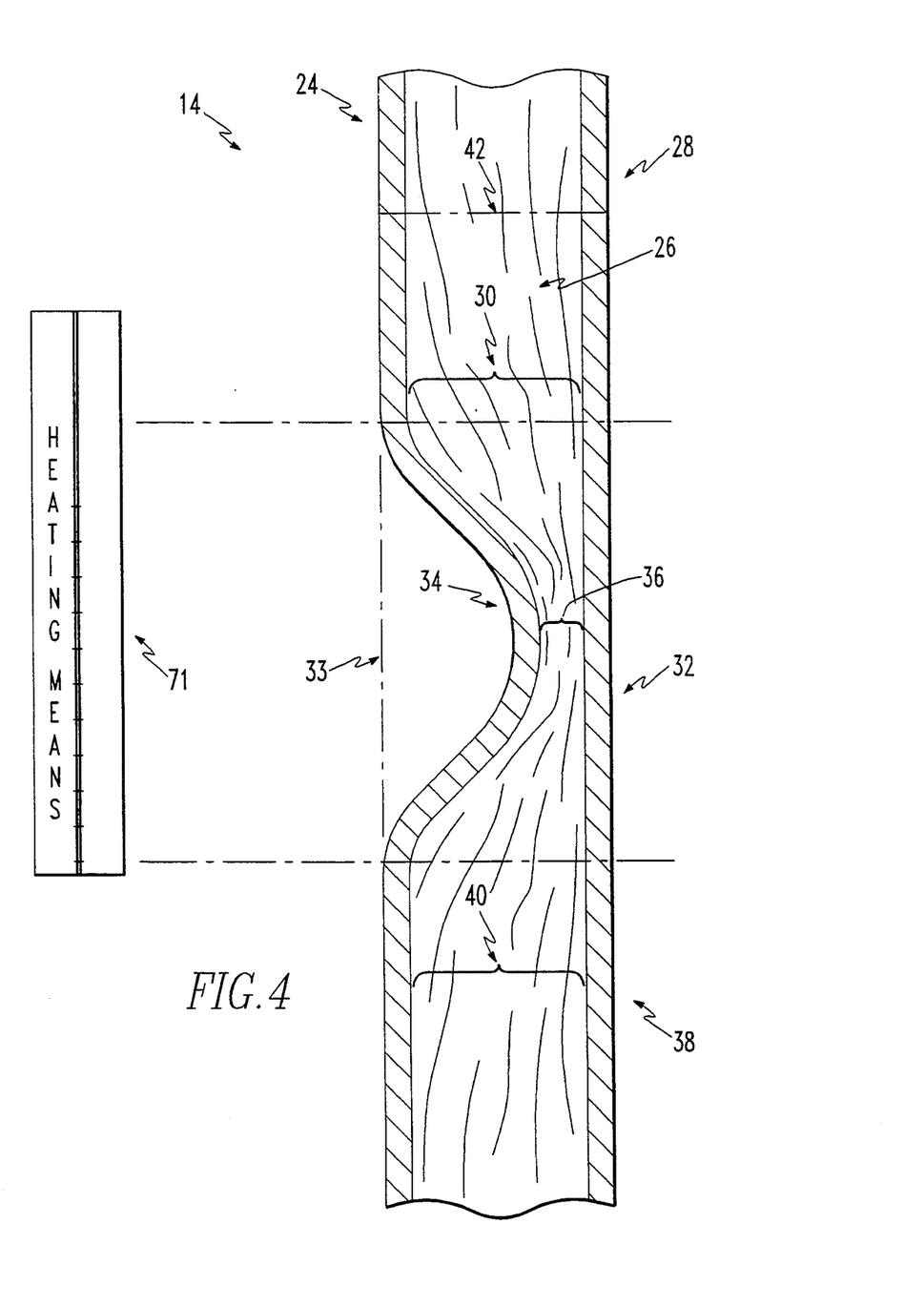
FIG. 4 is a schematic representation showing a cross section of a preferred embodiment of the restrictor.

In a preferred embodiment, and as shown in FIG. 4, restrictor 14 is comprised of a tubular member 24 having a channel 26. The tubular member 24 has a high pressure end (between 100-680 atmospheres) or first portion 28 in which the channel 26 has a first cross sectional area 30. There is also a second portion 32 for restricting the flow of fluid with analyte defined by a reproducible deformity 34 in the channel 26 such that the channel 26 has a second cross sectional area 36 which is smaller than the first cross sectional area 30 of the first portion 28. The tubular member 24 further defines a low pressure end (between 0-50 atmospheres) or third portion 38 having a third cross sectional area 40 which is greater than the second cross sectional area 36 of the second portion 32. The first portion 28 has essentially a constant outside diameter, represented by line 42 wherein all cross sectional dimensions of the tubular member 24 are less than or equal to the diameter of the first portion 28. The tubular member 24 defines an envelope 33. Preferably, the deformity 34 is defined by a spherical indentation and the tubular member 24 is comprised of stainless steel. A heating device 71, such as a resistive heater, can be in thermal communication with the tubular member 24. A more complete description of such a restrictor 14 can be found in U.S. patent application Ser. No. 07/828,729, filed Jan. 31, 1992, by D. Koebler, incorporated by reference.

Referring back to FIG. 1, the collecting device preferably also includes a device 46 for cryogenically cooling the collection trap 20 from ambient temperature to as low as $-180°$ C. or anywhere in-between, and a device 48 for heating the collection trap 20 and preferably, a device for ballistically heating the collection trap 20 to, for instance, at least 30° C. from $-40°$ C. within 90 seconds and preferably 20 seconds for LC analysis and to at least 275° C. from $-40°$ C. within 150 seconds and preferably 60 seconds for GC analysis. Even higher ramping rates to 1000° C./min. can be useful in making the analytes desorb in a very small "plug" from the trap. The cooling device 46 and the heating device 48 are in thermal communication with the collection trap 20. The collection trap 20 has a first end 66 where the fluid with analyte enters the collection trap 20 and a second end 68 where the fluid exits the collection trap 20.

The cooling device 46 preferably includes a device 50 for supplying liquid (carbon dioxide) $CO_2$ or liquid $N_2$ (nitrogen) about the collection trap 20 to cryogenically cool the collection trap 20. The heating device 48 preferably includes a coil disposed about the collection trap 20 to inductively or resistively heat the collection trap 20.

If a liquid chromatograph is used, N liquid reservoirs 52 are included, where N is an integer $\geq 1$. The liquid reservoirs 52 hold liquid solvent that deabsorbs analyte collected in the collection trap 20 and is the mobile phase for the liquid chromatograph 18. A liquid pump 54 is used for pumping the liquid in the reservoirs 52 to the collection trap 20 and a valve 82 for controlling flow of liquid solvent to the collection trap 20. The liquid pump 54 also serves as the pump for the liquid chromatograph 18. The liquid pump 54 and the liquid reservoirs 52 can be considered as part of the chromatograph 18 since they are needed for the chromatograph's 18 operation. The fluidic communication between the above-described elements is obtained by the use of tubing 58 in the system 10 that is preferably stainless steel.

Figure 3:
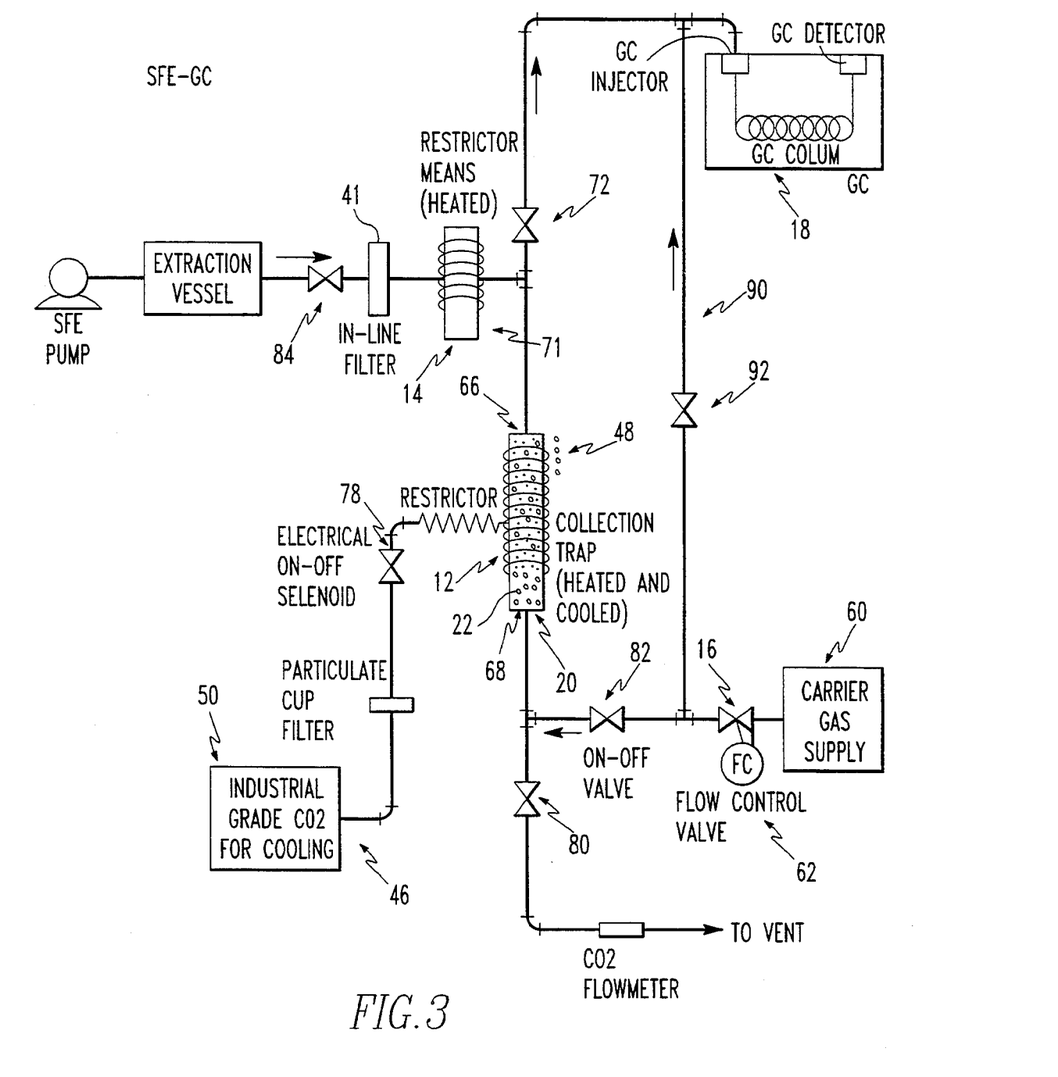
FIG. 3 is a schematic representation of the supercritical fluid extraction system with an on-line gas chromatograph, operating in a backflush mode.

Alternatively, if a gas chromatograph is used, a carrier gas supply 60 and a flow control valve 62 are used, as shown in FIG. 3. Preferably, there is also an alternate loop 90 between the chromatograph 18 and either the liquid pump 54 in LC mode or the gas flow control valve 62 in GC mode. The alternate loop 90 has a valve 92 for controlling the flow therethrough. The alternate loop 90 allows the chromatograph 18 to analyze a first sample while the collection device 12 collects a second sample. In this manner, the sampling cycle period of the chromatograph 18 is not limited by the collection device 12, since it can be operated independently therefrom.

Figure 2:
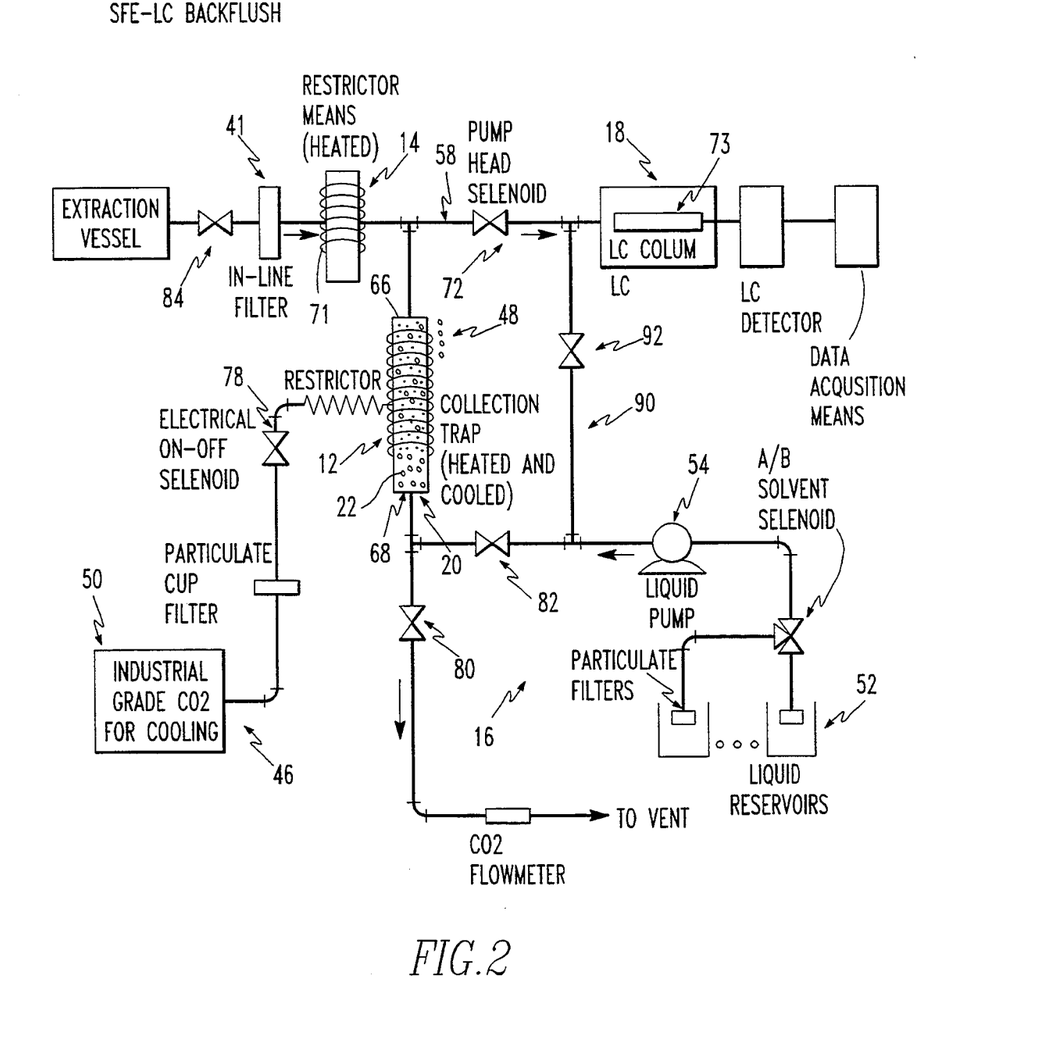
FIG. 2 is a schematic representation of a preferred embodiment of the supercritical fluid extraction system with an on-line liquid chromatograph, operating in a backflush mode.

In a preferred embodiment, it is desirable to deabsorb the analyte from the collection trap 20 in a direction opposite to the direction of flow of the supercritical fluid with analyte through the collection trap 20. When desorbing solvent flows in this manner through the collection trap 20, the analyte is being backflushed. This backflush embodiment allows the desorbed analytes to form a tighter plug to inject onto the chromatography column of the chromatograph 18. In this embodiment, which is shown in FIGS. 2 and 3, the chromatograph 18 is fluidically connected through the first end 66 of the collection trap 20. A valve 72 controls the flow of deabsorbing fluid to the chromatograph 18.

In an alternative embodiment of the collection system 10, and as shown in FIG. 1, the deabsorbing device 16 is fluidically connected to the collection trap 20 through the first end 66. In this manner, deabsorbing solvent flows in the same direction through the collection trap 20 as the fluid with analyte flows. When solvent flows in this manner through the collection trap 20, the analyte is being foreflushed. In this embodiment, the chromatograph 18 is fluidically connected to the second end 68 of the collection trap 20. A valve 70 disposed between the collection trap 20 and the chromatograph 18 controls the flow of fluid therebetween.

In the operation of the preferred embodiment, a backflush mode is used with respect to a liquid chromatograph as shown in FIG. 2. (It should be noted that the backflush mode is preferable when a gas chromatograph is used due to the need to keep the chromatographic peak as narrow as possible.) Pyrene analyte is extracted from a matrix, such as soil, by known supercritical fluid extraction techniques. The analyte which is dissolved in a solvent of supercritical $CO_2$ at 400 atmospheres and 100° C. temperature is provided to the restrictor 14 by way of 316 stainless steel tubing. The tubing passes through an in-line filter 41 which prevents plugging or clogging of the restrictor 14.

Referring to FIG. 4, the diameter 36 of the area 36 of the second portion 32 is between 5 microns and 20 microns in diameter. The control of flow through the second portion 32 results in a corresponding pressure drop such that analyte dissolved in the supercritical $CO_2$ passes therethrough to the low pressure third portion 38 having a pressure of about 1–50 atmospheres. After the $CO_2$ passes through the interface second portion 32, it is no longer supercritical. The second portion 32 is heated by heating means 44.

The low pressure third portion 38 of the restrictor 14 is fluidically connected to the collection trap 20 (refer to FIG. 2) by stainless steel tubing. The $CO_2$ with the analyte flows therethrough at a pressure of approximately 1 to 10 atmospheres. The restrictor 14 is maintained at 40° C. to 150° C. with heating means 71 such as a cartridge heater. A thermal couple in thermal contact with restrictor 14 senses the temperature of the restrictor 14 and controls the amount of heat provided thereto with the heating means 71. The heated restrictor 14 facilitates movement of fluid thereacross and minimizes its clogging.

The collection trap 20 is made of stainless and carbon steel for good heat transfer and is capable of withstanding pressures up to 65 atmospheres. The trap 20 has an inside diameter of 4.6 millimeters, a 174 inch outside diameter and is 7.5 centimeters long. The trap 20 is filled with silanized glass beads 22 of 100–120 mesh. The presence of the beads 22 increases the surface area upon which analyte can solidify as it passes through the collection trap 20. The collection trap 20 is cryogenically cooled with liquid $CO_2$. The collection trap 20 is able to be cooled within a two-minute period from ambient temperature to −50° C. or any set temperature in-between. The liquid $CO_2$ is provided by known techniques about the collection trap 20 and includes an on-off valve 78 to deliver the cooling $CO_2$.

The analyte essentially in its entirety precipitates from the depressurized fluid into the collection trap 20 and on the various surfaces in the collection trap 20. The $CO_2$ exits the collection trap 20 through valve 80 which is open. Valves 72 and 82 remains closed at this time.

After the analyte has been provided to the collection trap 20, valves 80 and 84 are closed, valves 72 and 82 are opened and the collection trap 20 is then ballistically heated from −50° C. to 40° C. within thirty seconds using inductive heating resistance coil 48. The liquid pump 54, fluidically connected to liquid reservoirs 52 containing organic liquid solvent at atmospheric pressure, is activated essentially at the same time that the collection trap 20 is ballistically heated and pumps the organic liquid solvent through the second end 68 of the collection trap 20.

As the solvent flows through the collection trap 20, the pyrene dissolves in the liquid solvent. The deabsorbing solvent continues through the collection trap 20 gathering the analyte, and then flows by way of stainless steel tubing to the liquid chromatograph 18 into the LC column 73. When essentially all of the analyte has been collected by the deabsorbing solvent after about 1 minute with a deabsorbing flow rate of 2 ml/min., valves 72 and 82 are then closed to isolate the liquid pump 54 and reservoirs 52 from the collection device 12. In turn, valve 92 is opened so that the organic liquid solvent is pumped, with liquid pump 54, through the alternate loop 90, directly to the chromatograph 18 to carry the analyte in the deabsorbing fluid in the LC column 73 through the chromatograph 18 for analysis. The chromatograph 18 analyzes the analyte in the liquid solvent to determine its composition, in this case, pyrene. Since the alternate loop 90 is remote from the collection trap 20, the collection trap 20 can collect analyte, while the chromatograph 18 analyzes a previous sample. In this case, valves 84 and 80 are open for allowing flow through the collection trap 20, while valves 82 and 72 are closed to isolate the alternate loop 90 from the collection device 20 loop.

If instead, a gas chromatograph 18 is used in backflush mode, as shown in FIG. 3, the operation is similar to the previously described process as illustrated in FIG. 2, but a carrier gas supply 60 and flow control valve 62 are used in place of the liquid reservoirs 52 and pump 54. The alternative loop 90 allows the gas chromatograph 18 to analyze the gas with analyte, while the collection trap 20 is collecting analyte from another sample.

Alternatively, as shown in FIG. 1, a foreflush mode can be used with the system 10 having a liquid chromatograph 18. During the collection step in foreflush mode, valves 84 and 80 are opened while valves 82 and 72 are closed. Then, to deabsorb the analyte from the collection trap 20, valves 84, 92 and 80 are closed and valves 82 and 72 are opened. After deabsorption of analyte is complete, if desired, the alternative loop 90 can be activated by opening valve 92 and closing valves 82 and 72. Valves 84 and 80 can be opened to allow the collection device 12 to operate on one sample while the chromatograph 18 analyzes the previous sample as described above.

Figure 5:
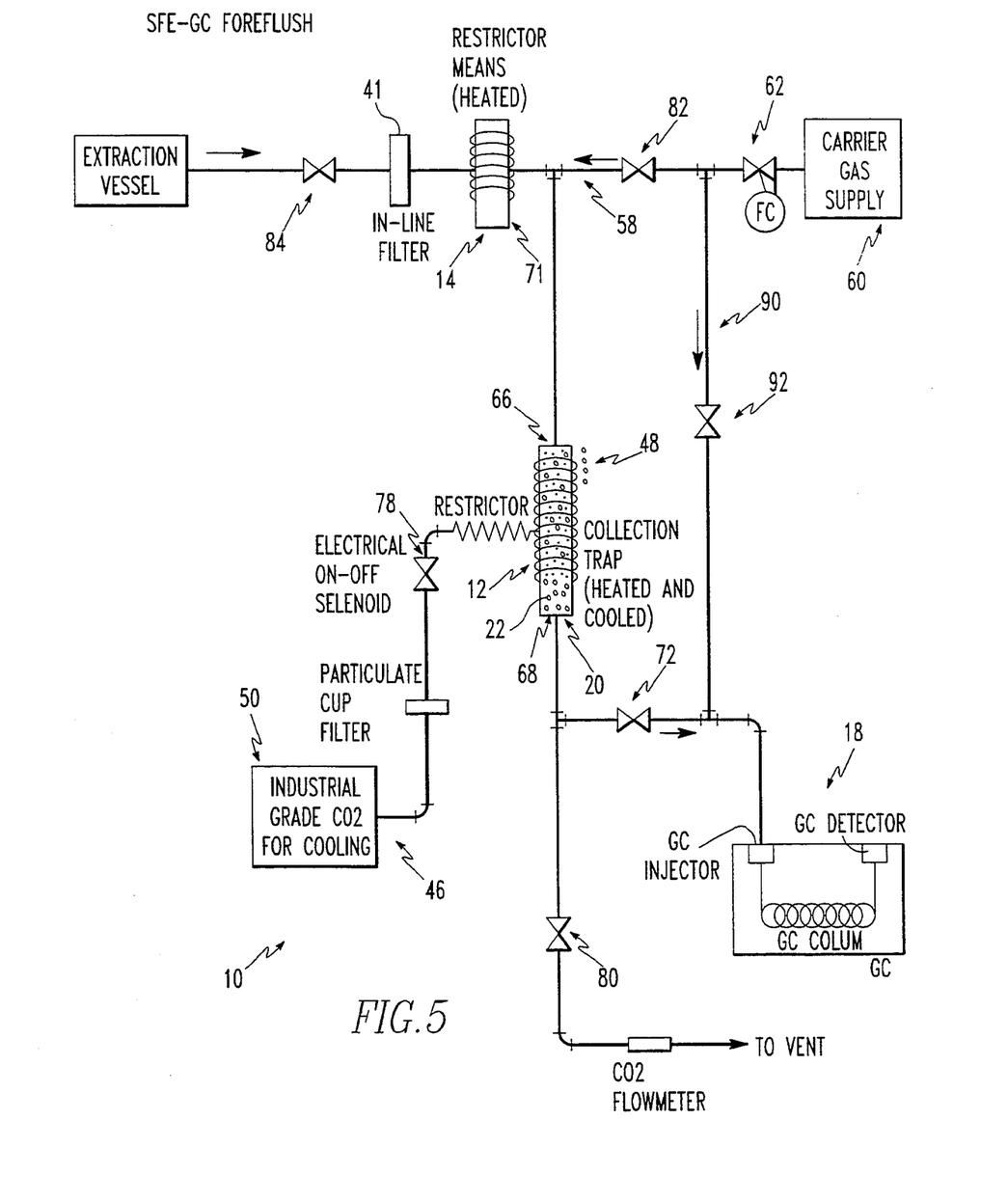
FIG. 5 is a schematic representation of the supercritical fluid extraction system with an on-line gas chromatograph, operating in a foreflush mode.

Alternatively, as shown in FIG. 5, a foreflush mode can be used with the system 10 having a gas chromatograph 18. The operation of this embodiment is similar to the previously described embodiment except that a flow control valve 62 and carrier gas supply 60 are used instead of the liquid pump 54 and reservoirs 52. The alternative loop 90 allows the gas chromatograph 18 to analyze the gas with analyte, while the collection trap 20 is collecting analyte from another sample.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A collection system for use with supercritical fluid extraction comprising:
    a device for collecting analyte from a fluid;
    a restrictor for controlling flow of fluid with analyte to the collecting device, said restrictor converting fluid with analyte from a first pressure to a second pressure, said second pressure less than said first pressure, said first pressure being a supercritical pressure, said restrictor in fluidic communication with said collecting device;
    a device for deabsorbing the analyte from the collecting device, said deabsorbing device in fluidic communication with said collecting device;
    a chromatograph for analyzing the analyte, said chromatograph in fluidic communication with said collecting device to receive deabsorbed analyte, said chromatograph remote from said collecting device; and
    an alternative loop for fluidically connecting the deabsorbing means to the chromatograph remotely from the device for collecting analyte such that the chromatograph can analyze a first sample while the collecting device simultaneously collects a second sample.

2. A system as described in claim 1 wherein the collecting device has a first end and a second end, said restrictor fluidically connected to the collecting device through the first end, said deabsorbing device in fluidic communication with the collecting device through the first end such that a deabsorbing fluid of the deabsorbing device flows from said first end to said second end.

3. A system as described in claim 2 wherein the chromatograph is in fluidic communication with the collecting device through the second end of the collecting device.

4. A system as described in claim 3 wherein the chromatograph includes a gas chromatograph.

5. A system as described in claim 3 wherein the chromatograph includes a liquid chromatograph.

6. A system as described in claim 1 wherein the collecting device has a first end and a second end, said restrictor fluidically connected to the connecting device through the first end, said deabsorbing device in fluidic communication with the collecting device through the second end such that a deabsorbing fluid of the deabsorbing device flows from said second end to said first end of said collecting device.

7. A system as described in claim 6 wherein the chromatograph is in fluidic communication with the collecting device through the first end of the collecting device.

8. A system as described in claim 7 wherein the chromatograph includes a gas chromatograph.

9. A system as described in claim 6 wherein the chromatograph includes a liquid chromatograph.

10. A system as described in claim 1 wherein said collecting device includes a collection trap in which analyte is gathered.

11. A system as described in claim 10 wherein the collecting device includes a device for cryogenically cooling the collection trap to at least $-180°$ C. and a device for heating the collection trap to at least $275°$ C. at a rate up to $1000°$ C./min., said cooling device and said heating device in thermal communication with said collection trap.

12. A system as described in claim 11 wherein the deabsorbing device includes N reservoirs, where N is an integer $\geq 1$, said liquid reservoirs holding deabsorbing fluid that deabsorbs analyte gathered in the collection trap and transports it to the chromatograph; said deabsorbing device also including a device for pumping the liquid in the reservoir to the collection trap, said pumping device in fluidic communication with said reservoir and said collection trap.

13. A system as described in claim 12 wherein said heating device includes a resistance coil disposed about the collection trap to inductively or resistively heat the trap.

14. A system as described in claim 13 wherein said cooling device includes a device for supplying liquid $CO_2$ about the collection trap to cryogenically cool the trap.

15. A system as described in claim 14 wherein the pumping device includes a pump in fluidic communication with the liquid reservoir.

16. A system as described in claim 15 wherein the collection trap includes absorbing beads disposed therein to increase the surface area upon which the analyte can be gathered.

17. A system as described in claim 16 wherein fluidic communications are obtained by steel tubing, and the collection trap is made of stainless steel.

18. A collection system as described in claim 1 wherein the deabsorbing device includes a liquid pump in fluidic communication with the collecting device and the chromatograph to provide fluid to the collecting device to deabsorb analyte in the collecting device and to provide fluid to the chromatograph to analyze the analyte.

* * * * *